(12) United States Patent
Schmitt et al.

(10) Patent No.: US 6,614,241 B2
(45) Date of Patent: Sep. 2, 2003

(54) CAPACITIVE SENSOR FOR DETECTING SURFACE CONDENSATION

(75) Inventors: Hans-Michael Schmitt, Muennerstadt (DE); Gottfried Berthold, Reutlingen (DE); Juergen Bach, Bad Neustadt/Saale (DE)

(73) Assignee: Preh-Werke GmbH & Co. KG, Saale (DE)

(*) Notice: Subject to any disclaimer, the term of this patent is extended or adjusted under 35 U.S.C. 154(b) by 70 days.

(21) Appl. No.: 09/818,779

(22) Filed: Mar. 28, 2001

(65) Prior Publication Data

US 2001/0030545 A1 Oct. 18, 2001

(30) Foreign Application Priority Data

Mar. 28, 2000 (DE) .......................... 100 15 430

(51) Int. Cl.$^7$ .............................. G01R 23/20
(52) U.S. Cl. ..................................... 324/664
(58) Field of Search ................ 324/664; 340/604; 430/309

(56) References Cited

U.S. PATENT DOCUMENTS

| | | |
|---|---|---|
| 3,671,913 A | 6/1972 | Mamiya et al. |
| 3,715,702 A | 2/1973 | Nichols |
| 4,639,831 A | 1/1987 | Iyoda |
| 4,696,796 A | 9/1987 | Oka et al. |
| 5,959,535 A * | 9/1999 | Remsburg .............. 340/604 |
| 5,965,326 A * | 10/1999 | Ellis .......................... 430/309 |

FOREIGN PATENT DOCUMENTS

| | | |
|---|---|---|
| DE | 19708053 | 9/1998 |
| DE | 19708053 A | 9/1998 |
| DE | 19746989 | 5/1999 |
| JP | 60211346 A | 3/1986 |
| WO | WO98/38499 * | 9/1998 |

* cited by examiner

*Primary Examiner*—Christine K. Oda
(74) *Attorney, Agent, or Firm*—Birch, Stewart, Kolasch & Birch, LLP

(57) ABSTRACT

A capacitive sensor for detecting surface condensation which includes a carrier (2), a metal layer (3) applied to the carrier (2) to form an interdigital structure, a passivation layer (6) formed over the metal layer (3), and a hydrophilic layer (7) applied over the passivation layer (6), where the hydrophilic layer (7) increases a surface tension of the passivation layer (7).

18 Claims, 1 Drawing Sheet

CAPACITIVE SENSOR FOR DETECTING SURFACE CONDENSATION

This application claims priority to German patent application 100 15 430.1, filed Mar. 28, 2000. The entire content thereof is incorporated herein by reference.

BACKGROUND OF THE INVENTION

1. Field of the Invention

The present invention relates to capacitive sensors for detecting surface condensation.

2. Related Art

Sensors are often used to detect incipient moisture on automotive windshields. These sensors may be used to detect condensation on the surface of a windshield, and by analyzing signals generated by the sensors, it is possible to take measures to reduce the condensation.

Such a sensor is described in German Patent Application DE 197 080 53 A1. The patented sensor includes a carrier layer onto which is applied a metal layer as an interdigital structure, thereby forming a capacitor. A temperature-dependent resistor that is integrated into the capacitor is also used simultaneously as a temperature sensor and as a heating sensor. In addition to a passivation layer, an additional layer that promotes moisture condensation is applied to the carrier layer. Nuclei of condensation, i.e., irregularities at which condensation of moisture begins, are integrated into this additional layer.

However, the known device has a specific disadvantage. In particular, the device does not readily achieve a uniform water film formation, which accurately indicates the formation of condensation. Instead, as condensation beings (nuclei of condensation), droplet-like moisture forms having an irregular formation, which thus reduces the sensitivity of the sensor.

SUMMARY OF THE INVENTION

The object of this invention is to provide a generic sensor, which has a greater sensitivity.

The object of the present invention is achieved by treating the surface of a passivation layer applied over an interdigital capacitor in a controlled manner, to increase the surface energy or surface tension. This eliminates having to use an additional layer with condensation nuclei. Therefore, moisture condensation molecules can develop anywhere on the surface, causing a change in the capacitance of the interdigital capacitor at any point on the surface.

The surface is preferably prepared by applying a hydrophilizing agent to produce a hydrophilic layer applied to the passivation layer. The hydrophilic layer is preferably applied using a dipping or spraying method.

The advantageous effects of the present invention include better feed through of an electric field due to the moisture, an improvement in uniform water condensation at the start of the condensation of moisture, and the development of a continuous film of water.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
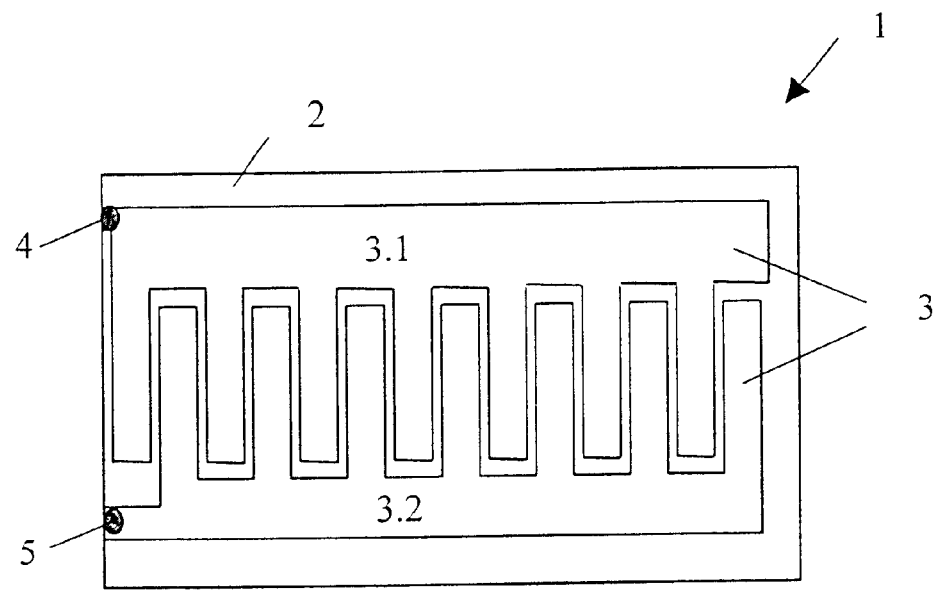
FIG. 1 illustrates a capacitive sensor with an interdigital structure.

FIG. 1 illustrates a capacitive sensor 1 having a carrier 2. A metal layer 3 having a thickness of approximately 5 $\mu$m is applied to the carrier 2 to form interdigital structure 3.1, 3.2. The interdigital structure 3.1, 3.2 forms the capacitor. To allow an analyzer unit (not shown here) to receive signals from the sensor 1, the sensor 1 includes bond islands 4, 5 on the edge of interdigital structure 3.1, 3.2, which may be interfaced with such an analyzer unit.

Figure 2:
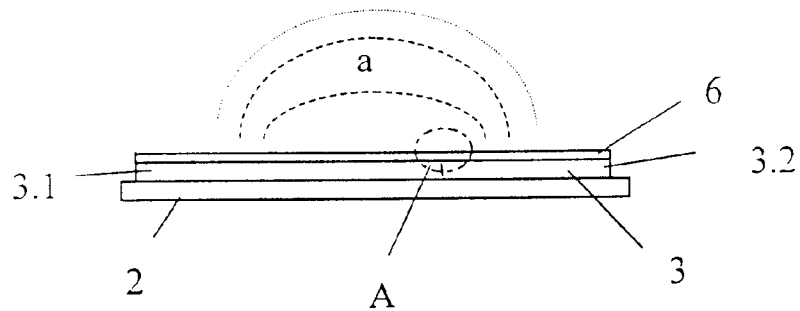
FIG. 2 illustrates the sensor shown in FIG. 1, with an applied hydrophilizing agent, according to an embodiment of the present invention.

As is shown in FIG. 2, a passivation layer 6 is applied to the metal layer 3. The passivation layer 6 is preferably a thin film overglaze layer ($SiO_x$), and preferably has a thickness of approximately 1 $\mu$m. A feed through of field lines (a) from one interdigital structure half 3.1 to the other interdigital structure half 3.2 is realized by way of the overglaze layer 6.

The passivation layer 6 is made hydrophilic to increase the sensitivity of the sensor 1. In particular, the surface energy of the layer 6 is increased by applying a hydrophilic layer 7 having a thickness of approximately 0.01 $\mu$m. Applying the hydrophilic layer may be accomplished with a dipping or spraying method. However, other conventional application methods may also be used. This creates a condensation surface that is highly hydrophilic. Therefore, water molecules of condensation 8 cover the entire area of the hydrophilic layer 7 and thus also cover the overglaze layer 6.

Figure 3:
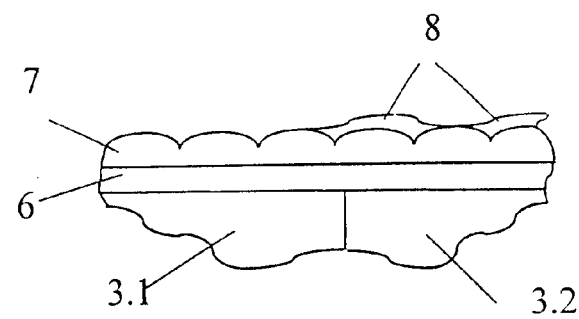
FIG. 3 illustrates an exploded view of the hydrophilic layer shown in FIG. 2.

FIG. 3 illustrates an exploded view of the hydrophilic layer 7. The hydrophilic layer 7 is positioned over the entire surface of the overglaze layer 6, and/or covers the entire surface of the hydrophilic layer 7. Due to the uniform hydrophilic layer 7, incipient condensation of moisture 8 develops uniformly over the entire surface regardless of the nuclei of condensation. Therefore, a change in the capacitance of the capacitor occurs. This change takes place at any location on the surface of the overglaze layer 6 where condensation of moisture 8 begins. As a result of the change in capacitance, a change in the signals at pickups 4, 5 occurs, and the signals are sent to the analyzer unit for analysis.

The carrier material 2 is preferably made of a flexible material.

A known resistance arrangement may also be integrated into sensor 1.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A capacitive sensor for detecting surface condensation, comprising:

a carrier;

a metal layer applied to the carrier to form an interdigital structure;

a passivation layer formed over the metal layer; and a hydrophilic layer being applied over the passivation layer through dipping or spraying, wherein the hydrophilic layer increases a surface tension of the passivation layer such that a uniform water film formation is achieved.

2. The sensor according to claim 1, wherein the passivation layer is an overglaze layer.

3. The sensor according to claim 1, wherein the hydrophilic layer has a thickness of 0.01 $\mu$m.

4. The sensor according to claim 1, wherein the hydrophilic layer promotes wetting.

5. The sensor according to claim 1, wherein the hydrophilic layer is a plied by way of spraying.

6. The sensor according to claim 1, wherein the hydrophilic layer is a plied by way of dipping.

7. A capacitive sensor, comprising:

a carrier member;

a first layer formed over the carrier member; and a hydrophilic layer applied being over the first layer through dipping or spraying, the hydrophilic layer increasing a surface tension of the first layer such that a uniform water film formation is achieved.

8. The sensor according to claim 7, further comprising a metal layer formed over the carrier member.

9. The sensor according to claim 8, wherein the metal layer is applied directly to the carrier member.

10. The sensor according to claim 7, wherein the first layer is a passivation layer.

11. The sensor according to claim 10, wherein the passivation layer is an overglaze layer.

12. The sensor according to claim 7, further comprising an intermediate layer formed between the carrier member and the first layer, the intermediate layer being applied directly to the carrier and the first layer being directly applied directly to the intermediate layer.

13. The sensor according to claim 7, wherein the hydrophilic layer is applied directly to the first layer.

14. A method for providing a manufacturing a capacitive sensor, comprising the steps of:

(a) providing a carrier member;

(b) forming a metal layer over the carrier member;

(c) forming a passivation layer over the carrier member; and (d) forming a hydrophilic layer over the passivation layer through dipping or spraying, wherein the hydrophilic layer increases a surface tension of the passivation layer such that a uniform water film formation is achieved.

15. The method according to claim 14, wherein step (b) forms the metal layer over and directly on the carrier member.

16. The method according to claim 14, wherein step (c) forms the passivation layer over and directly on the metal layer.

17. The method according to claim 14, wherein step (d) forms the hydrophilic layer directly on the passivation layer.

18. A capacitive sensor for detecting surface condensation, comprising:

a carrier having a metal layer applied to the carrier to form an interdigital structure, which forms the capacitor for the sensor; and a passivation layer formed over the metal layer, wherein a hydrophilic layer is applied over the passivation layer through dipping or spraying, through which a surface tension of the passivation layer is increased.

* * * * *